(12) United States Patent
Gaier et al.

(10) Patent No.: US 6,579,711 B1
(45) Date of Patent: Jun. 17, 2003

(54) LACTIC ACID BACTERIA SPECIES

(75) Inventors: Walter Gaier, Chailly/Montreux (CH); David Pridmore, Lausanne (CH); Francesca Stingele, St-Prex (CH); Jean-Richard Neeser, Savigny (CH); Patrice Desachy, Porsel FR (CH); Bruno Pot, Sint-Michiels Brugge (BE)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/548,606

(22) Filed: Apr. 13, 2000

Related U.S. Application Data (63) Continuation of application No. PCT/EP98/06636, filed on Oct. 9, 1998.

(30) Foreign Application Priority Data

Oct. 17, 1997 (EP) ............................................ 97203245

(51) Int. Cl.⁷ ............................ A01N 63/00; C12N 1/20
(52) U.S. Cl. ............................... 435/253.4; 435/252.1; 435/252.9; 435/883; 435/884; 424/93.4; 424/93.44; 424/93.45
(58) Field of Search .................. 426/84, 86; 424/93.44, 424/93.45, 93.4; 435/253.4, 252.9, 252.1, 885, 853

(56) References Cited

U.S. PATENT DOCUMENTS

| | | | | |
|---|---|---|---|---|
| 3,875,305 A | * | 4/1975 | Storrs | 426/38 |
| 4,601,985 A | * | 7/1986 | Okonogi et al. | 426/253 |
| 6,056,979 A | * | 5/2000 | Benbadis et al. | 426/34 |

FOREIGN PATENT DOCUMENTS

| | | | |
|---|---|---|---|
| SU | 362610 | * | 12/1972 |
| SU | 1412699 | * | 7/1988 |

OTHER PUBLICATIONS

Snaidr et al. Appl. Environ. Microbiol. 1997. 63(7), 2884–2896.*
Talaro et al. "Foundations in Microbiology". WCB C, Browm Publishers. 1993. p. 171.*
STS database GENBANK.RTM. GenBank ACC. No. (GBN) : Z94012. Apr. 15, 1997.*
Jermini et al., "The Microbiology of Home–Made Style Formaggini Fresh Cheese Manufactured in Southern Switzerland Incidence of Enterotoxigenic Strains of *Staphylococcus–Aureus* and *Escherichia–Coli*", Mitt Geb Levensmittelunters Hyg 81 (6) : 633–654 (1990).*
Hamana et al., "Distribution of Spermine in Bacilli and Lactic Acid Bacteria", Can. J. Microbiol. 35 (4) : 450–455 (1989).*
Averina et al., "DNA Homology among Strains of Thermophilic and Mesophilic Streptococci Obtained from Different Sources", Midrobiologiya 67 (6) : 792–798 (1998).*

\* cited by examiner

*Primary Examiner*—Jon P. Weber
*Assistant Examiner*—Vera Afremova
(74) *Attorney, Agent, or Firm*—Winston & Strawn (57) ABSTRACT

Strain of lactic acid bacterium, (1) whose 16S ribosomal RNA is characteristic of the genus Streptococcus, (2) whose total protein profile, obtained after migration of the total proteins on an SDS-PAGE electrophoresis gel, is characteristic of that of the strain of lactic acid bacterium CNCM I-1920 but distinct from those of the recognized species belonging to the genus Streptococcus, namely *S. acidominimus, S. agalactiae, S. alactolyticus, S. anginosus, S. bovis, S. canis, S. caprinus, S. constellatus, S. cricetus, S. cristatus, S. difficile, S. downei, S. dysgalactiae* ssp. *dysgalactiae, S. dysgalactiae* ssp. *equisimilis, S. equi, S. equi* ssp. *equi, S. equi* ssp. *zooepidemicus, S. equinus, S. ferus, S. gallolyticus, S. gordonii, S. hyointestinalis, S. hyovaginalis, S. iniae, S. intermedius, S. intestinalis, S. macacae, S. mitis, S. mutans, S. oralis, S. parasanguinis, S. parauberis, S. phocae, S. pleomorphus, S. pneumoniae, S. porcinus, S. pyogenes, S. ratti, S. salivarius, S. sanguinis, S. shiloi, S. sobrinus, S. suis, S. thermophilus, S. thoraltensis, S. uberis, S. vestibularis, S. viridans*. The invention also relates to the use of a strain of lactic acid bacterium according to the invention, or of a polysaccharide secreted by a strain according to the invention, for the preparation of a dietary composition, in particular an acidified milk or a fromage frais. The invention also relates to a dietary or pharmaceutical composition comprising a strain of lactic acid bacterium or a polysaccharide consisting of a succession of glucose, galactose and N-acetylglucosamine in a respective proportion of 3:2:1. In particular, strains CNCM I-1920, I-1921, I-1922, I-1923, I-1924, I-1925 and I-1926.

18 Claims, 2 Drawing Sheets

SEQUENCE LISTING

<160> NUMBER OF SEQ ID NOS: 3

<210> SEQ ID NO 1
<211> LENGTH: 1522
<212> TYPE: DNA
<213> ORGANISM: Bacteria
<220> FEATURE:
<221> NAME/KEY: misc_feature
<222> LOCATION: (1)...(1522)
<223> OTHER INFORMATION: n = A,T,C or G

<400> SEQUENCE: 1

```
gtcgacagag ttcgatcctg gctcaggacg aacgctggcg gcgtgcctaa tacatgcaag      60
tagaacgctg aagactttag cttgctagag ttggaagagt tgcgaacggg tgagtaacgc     120
gtaggtaacc tgcctattag tgggggataa ctattggaaa cgatagctaa taccgcataa     180
tagtgtttaa cacatgttag agacttaaaa gatgcaattg catcactagt agatggacct     240
gcgttgtatt agctagttgg tgggtaacg gcctaccaag gcgacgatac atagccgacc     300
tgagagggtg atcggccaca ctgggactga gacacggccc agactcctac gggaggcagc     360
agtagggaat cttcggcaat ggggggcaacc tgaccgagca acgccgcgtg agtgaagaag     420
gttttcggat cgtaaagctc tgttgtaaga gaagaacgtg tgtgagagtg gaaagttcac     480
acagtgacgg taacttacca gaaagggacg gctaactacg tgccagcagc cgcggtaata     540
cgtaggtccc gagcgttgtc cggatttatt gggcgtaaag cgagcgcagg cggttttaata    600 agtctgaagt taaggcagt ggcttaacca ttgttcgctt tggaaactgt taaacttgag     660
tgcagaaggg gagagtggaa ttccatgtgt agcggtgaaa tgcgtagata tatggaggaa     720
caccggtggc gaaagcggct ctctggtctg taactgacgc tgaggctcga aagcgtgggg     780
agcaaacagg attagatacc ctggtagtcc acgccgtaaa cgatgagtgc taggtgttag     840 gcccttttccg gggcttagtg ccgcagctaa cgcattaagc actccgcctg gggagtacga     900
ccgcaaggtt gaaactcaaa ggaattgacg ggggccgcac aagcggtgga gcatgtggtt     960
taattcgaag caacgcgaag aacttaccag gtcttgacat cccgatgcta tttctagaga    1020
tagaaagttt cttcggaaca tcggtgacag gtggtgcatg gttgtcgtca gctcgtgtcg    1080
tgagatgttg ggttaagtcc cgcaacgagc gcaacccccta ttgttagttg ccatcattca    1140
gttgggcact ctagcgagac tgccggtgat aaaccggagg aaggtgggga tgacgtcaaa    1200
tcatcatgcc ccttatgacc tgggctacac acgtgctaca atggttggta caacgagtcg    1260
caagccggtg acggcaagca aatctcttaa agccaatctc agttcggatt gtaggctgca    1320
actcgcctac atgaagtcgg aatcgctagt aatcgcggat cagcacgccg cggtgaatac    1380
gttcccgggc cttgtacaca ccgcccgtca caccacgaga gttttgtaaca cccgaagtcg    1440 gtgaggtaac ctttttaggan ccagccgcct aaggtgggac agatgattgg ggtgaagtcg    1500
taacaaggta accgtaggat cc                                              1522
```

<210> SEQ ID NO 2
<211> LENGTH: 34
<212> TYPE: DNA
<213> ORGANISM: Oligonucleotide
<220> FEATURE:
<223> OTHER INFORMATION: Primer

<400> SEQUENCE: 2

```
atatccgttt tttcgacaga gttygatyct ggct                                   34
```

```
<210> SEQ ID NO 3
<211> LENGTH: 33
<212> TYPE: DNA
<213> ORGANISM: Oligonucleotide
<220> FEATURE:
<223> OTHER INFORMATION: Primer

<400> SEQUENCE: 3
atatccggat cctacggyta ccttgttacg act                              33
```

LACTIC ACID BACTERIA SPECIES

CROSS-REFERENCE TO RELATED APPLICATIONS

This application is a continuation of the U.S. phase of co-pending International Application No. PCT/EP98/06636, filed Oct. 9, 1998, the content of which is expressly incorporated herein by reference thereto.

FIELD OF THE INVENTION

The present invention relates to new species of lactic acid bacteria belonging to the genus Streptococcus.

BACKGROUND OF THE INVENTION

The identification of lactic acid bacteria is essential in the dairy industry, and consists in differentiating distinctive morphological, physiological and/or genetic characteristics between several species.

The distinctive physiological characteristics for a given species of lactic acid bacteria may be determined by various tests including, for example, analyzing their capacity to ferment various sugars and the migration profile of total proteins on an SDS-PAGE type electrophoresis gel (Pot et al., Taxonomy of lactic acid bacteria, in Bacteriocins of lactic acid bacteria, Microbiology, Genetics and Applications, L. De Vuyst, and E. J. Vandamme ed., Blackie Academic & Professional, London, 1994).

The migration profile of the total proteins of a given species, determined by SDS-PAGE gel electrophoresis, when compared, with the aid of a densitometer, with other profiles obtained from other species, makes it possible to determine the taxonomic relationships between the species. Numerical analysis of the various profiles, for example, with the GelCompar® software, makes it possible to establish the degree of correlation between the species which is a function of various parameters, in particular of the algorithms used (GelCompar, version 4.0, Applied Maths, Kortrijk, Belgium; algorithms: "Pearson Product Moment Correlation Coefficient, Unweighted Pair Group Method Using Average Linkage").

To date, comparative analysis of the total protein profile by SDS-PAGE gel electrophoresis has been thoroughly tested as an effective means for distinguishing between homogeneous and distinct groups of species of lactic acid bacteria (Pot et al., Chemical Methods in Prokaryotic Systematics, Chapter 14, M. Goodfellow, A. G. O'Donnell, Ed., John Wiley & Sons Ltd, 1994).

With this SDS-PAGE method, the preceding experiments have thus shown that when a degree of Pearson correlation of more than 78 (on a scale of 100) is obtained between two strains of lactic acid bacteria, it is justifiably possible to deduce therefrom that they belong to the same species (Kersters et al., Classification and Identification methods for lactic bacteria with emphasis on protein gel electrophoresis, in Acid Lactic Bacteria, Actes du Colloque Lactic '91, 33–40, Adria Normandie, France, 1992; Pot et al., The potential role of a culture collection for identification and maintenance of lactic acid bacteria, Chapter 15, pp. 81–87, in: The Lactic Acid Bacteria, E. L. Foo, H. G. Griffin, R. Mollby and C. G. Heden, Proceedings of the first lactic computer conference, Horizon Scientific Press, Norfolk).

By way of example, it was recently possible to divide the group of acidophilic lactic acid bacteria into 6 distinct species by means of this technique (Pot et al., *J General Microb.*, 139, 513–517, 1993). Likewise, this technique was recently used to establish, in combination with other techniques, the existence of several new species of Streptococcus, such as *Streptococcus dysgalactiae* subsp. *equisimilis*, *Streptococcus hyovaginalis* sp. *nov.* and *Streptococcus thoraltensis* sp. *nov* (Vandamme et al., *Int. J. Syst. Bacteriol.*, 46, 774–781, 1996; Devriese et al., *Int. J. Syst. Bacteriol.*, 1997, In press).

The identification of new species of lactic acid bacteria cannot however be reduced to a purely morphological and/or physiological analysis of the bacteria. Indeed, two species which are very closely related morphologically and/or physiologically may be distantly related from a genetic point of view. Analysis of the 16S ribosomal RNA of the lactic acid bacteria is thus of vital importance for determining definitively if a lactic acid bacterium belongs to a known genus or species.

To date, the "Deutsche Sammlung Von Mikroorganismen und Zellkulturen GmbH" (DSM, Braunschweig, Germany) has officially recorded about 48 different species belonging to the genus Streptococcus (see the list below). All these species possess a 16S ribosomal RNA which is typical of the genus Streptococcus, and may be divided into distinct and homogeneous groups by means of the SDS-PAGE technique mentioned above.

The present invention relates to the identification, by means of the techniques presented above, of a new species of lactic acid bacterium belonging to the genus Streptococcus, and to its use in the dairy industry in general.

SUMMARY OF THE INVENTION

The invention relates to any lactic acid bacterium, whose 16S ribosomal RNA is characteristic of the genus Streptococcus; and whose total protein profile, obtained after migration of the total proteins on an SDS-PAGE electrophoresis gel, is characteristic of that of the strain of lactic acid bacterium CNCM I-1920, but distinct from those of the recognized species belonging to the genus Streptococcus, namely *S. acidominimus, S. agalactiae, S. alactolyticus, S. anginosus, S. bovis, S. canis, S. caprinus, S. constellatus, S. cricetus, S. cristatus, S difficile, S. downei, S. dysgalactiae* ssp. *dysgalactiae, S. dysgalactiae* ssp. *equisimilis, S equi, S. equi* ssp. *equi, S equi* ssp. *zooepidemicus, S. equinus, S. ferus, S. gallolyticus, S gordonii, S. hyointestinalis, S. hyovaginalis, S. iniae, S. intermedius, S intestinalis, S. macacae, S. mitis, S. mutans, S. oralis, S. parasanguinis, S. parauberis, S. phocae, S. pleomorphus, S. pneumoniae, S. porcinus, S pyogenes, S. ratti, S. salivarius, S. sanguinis, & shiloi, S sobrinus, S. suis, S thermophilus, S. thoraltensis, S. uberis, S. vestibularis, S. viridans*.

The invention further relates to the use of a strain of lactic acid bacterium according to the invention for the preparation of a dietary composition, in particular an acidified milk or a fromage frais, for example.

The invention also relates to the use of a polysaccharide, capable of being secreted by a lactic acid bacterium according to the invention, which consists of a chain of glucose, galactose and N-acetylglucosamine in a respective proportion of 3:2:1, for the preparation of a dietary or pharmaceutical composition.

The subject of the invention is a dietary or pharmaceutical composition comprising a strain of lactic acid bacterium according to the invention.

Finally, the subject of the invention is also a dietary or pharmaceutical composition comprising a polysaccharide consisting of a chain of glucose, galactose and N-acetylglucosamine in a respective proportion of 3:2:1.

DETAILED DESCRIPTION OF THE INVENTION

The attachment of the new species of the invention to the genus Streptococcus is preferably demonstrated by comparing the nucleotide sequence of the 16S ribosomal RNA of the bacteria of the invention, or of their genomic DNA which codes for the 16S ribosomal RNA, with those of other genera and species of lactic acid bacteria known to date.

More particularly, it is possible to use the method disclosed in Example 1 below, or alternatively other methods known to a person skilled in the art, for example, Schleifer et al., *System. Appl. Microb.*, 18, 461–467, 1995; Ludwig et al., *System. Appl. Microb.*, 15, 487–501, 1992. The nucleotide sequence SEQ ID NO: 1 presented in the sequence listing below is characteristic of this new species, and exhibits striking similarities with the 16S ribosomal RNA sequences found in the species of Streptococcus recognized to date.

The new species according to the invention, which constitutes a distinct and homogeneous new group, can also be differentiated from the other known species belonging to the genus Streptococcus by means of the technique for identification of the total proteins by SDS-PAGE gel electrophoresis, described above.

In particular, this new species may give a total protein profile, obtained after culture of the bacterium in an MRS medium for 24 h at 28° C., extraction of the total proteins and migration of the proteins on an SDS-PAGE electrophoresis gel, which exhibits a degree of Pearson correlation of at least 78 (on a scale of 100) with the profile obtained under identical conditions with the strain of lactic acid bacterium CNCM I-1920, and this with respect to the profiles obtained under identical conditions with a few of the various species of lactic acid bacteria, in particular those indicated below, for example. More particularly, this technique consists in (1) isolating all the proteins (=total proteins) of a culture of lactic acid bacterium cultured under defined conditions, (2) separating the proteins by electrophoresis on an SDS-PAGE gel, (3) analyzing the arrangement of the different protein fractions separated with the aid of a densitometer which measures the intensity and the location of each band, (4) and comparing the protein profile thus obtained with those of several other species of Streptococcus which have been obtained, in parallel or beforehand, under exactly the same operating conditions.

The techniques for preparing a total protein profile as described above, as well as the numerical analysis of such profiles, are well known to a person skilled in the art. However, the results are only reliable insofar as each stage of the process is sufficiently standardized.

Faced with this requirement, standardized procedures are regularly made available to the public by their authors such as that of Pot et al., as presented during a "workshop" organized by the European Union, at the University of Ghent, in Belgium, on Sep. 12 to 16, 1994 (Fingerprinting techniques for classification and identification of bacteria, SDS-PAGE of whole cell protein). The software used in the technique for analyzing the SDS-PAGE electrophoresis gel is of crucial importance since the degree of correlation between the species depends on the parameters and algorithms used by this software. Without going into the theoretical details, quantitative comparison of bands measured by a densitometer and normalized by a computer is preferably made with the Pearson correlation coefficient. The similarity matrix thus obtained may be organized with the aid of the UPGMA (unweighted pair group method using average linkage) algorithm that not only makes it possible to group together the most similar profiles, but also to construct dendograms (see K. Kersters, Numerical methods in the classification and identification of bacteria by electrophoresis, in Computer-assisted Bacterial Systematics, 337–368, M. Goodfellow, A. G. O'Donnell Ed., John Wiley and Sons Ltd, 1985).

Preferably, the strains of the new species exhibit a total protein profile having a degree of Pearson correlation of at least 85 with respect to one of the strains of bacteria of the new species. For the biotypes mentioned below, this degree of Pearson correlation can even exceed 90, for example.

By means of the SDS-PAGE electrophoresis gel technique for identification, the new species according to the invention that belong to the genus Streptococcus may be distinguished from all the species of Streptococcus recognized to date, namely *S. acidominimus, S. agalactiae, S. alactolyticus, S. anginosus, S. bovis, S. canis, S. caprinus, S. constellatus, S. cricetus, S. cristatus, S. difficile, S. downei, S. dysgalactiae* ssp. *dysgalactiae, S. dysgalactiae* ssp. *equisimilis, S. equi, S. equi* ssp. *equi, S. equi* ssp. *zooepidemictus, S. equinus, S. ferus, S. gallolyticus, S. gordonii, S. hyointestinalis, S. hyovaginalis, S. iniae, S. intermedius, S. intestinalis, S. macacae, S. mitis, S. mutans, S. oralis, S. parasanguinis, S. parauberis, S. phocae, S. pleornorphus, S. pneumoniae, S. porcinus, S. pyogenes, S. ratti, S. salivarius, S. sanguinis, S. shiloi, S. sobrinus, S. suis, S. thermophilus, S. thoraltensis, S. uberis, S. vestibularis,* and *S. viridans.*

The new species according to the invention can also be distinguished by this technique from the lactic acid bacteria which had been previously classified in error in the genus Streptococcus such as *S. adjacens* (new classification= *Abiotrophia adiacens*), *S. casseliflavus* (=*Enterococcus casseliflavus*), *S. cecorum* (=*Enterococcus cecorum*), *S. cremoris* (=*Lactococcus lactis* subsp. *cremoris*), *S. defectivus* (=*Abiotrophia defectiva*), *S. faecalis* (=*Enterococcus faecalis*), *S. faecium* (=*Enterococcus faecium*), *S. gallinarum* (=*Enterococcus gallinarum*), *S. garvieae* (=*Lactococcus garvieae*), *S. hansenii* (=*Ruminococcus hansenii*), *S. lactis* (=*Lactococcus lactis* subsp. *lactis*), *S. lactis cremoris* (=*Lactococcus lactis* subsp. *cremoris*), *S. lactis diacetilactis* (=*Lactococcus lactis* subsp. *lactis*), *S. morbillorum* (=*Gemella morbillorum*), *S. parvulus* (=*Atopobium parvulum*), *S. plantarum* (=*Lactococcus plantarum*), *S. raffinolactis* (=*Lactococcus raffinolactis*) and *S. saccharolyticus* (=*Enterococcus saccharolyticus*).

The lactic acid bacteria according to the invention have a morphology characteristic of *Lactococcus lactis*, for example; that is to say that they have the shape of cocci assembled into chains.

The sugars which can be fermented by the new species are generally at least one of the following; D-galactose, D-glucose, D-fructose, D-mannose, N-acetyl-(D)-glucosamine, salicin, cellobiose, maltose, lactose, sucrose and raffinose.

Among all the strains of the new species which have been isolated in dairies in Switzerland, 7 were deposited under the treaty of Budapest, by way of example, in the Collection Nationale de Culture de Microorganismes (CNCM), 25 rue du docteur Roux, 75724 Paris, on Oct. 14, 1997, where they were attributed the deposit numbers CNCM I-1920, I-1921, I-922, I-1923, I-1924, I-1925 and I-1926.

The strains of the new species can be used, for example, to prepare a dietary or pharmaceutical product, in particular in the form of a fresh, concentrated or dried culture.

Milk-based products are obviously preferred within the framework of the invention. Milk is however understood to mean that of animal origin, such as cow, goat, sheep, buffalo, zebra, horse, donkey, or camel, and the like. The milk may be in the native state, a reconstituted milk, a skimmed milk or a milk supplemented with compounds necessary for the growth of the bacteria or for the subsequent processing of fermented milk, such as fat, proteins of a yeast extract, peptone and/or a surfactant, for example. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

Pharmaceutical products means products intended to be administered orally, or even topically, which comprise an acceptable pharmaceutical carrier to which, or onto which, a culture of the new species is added in fresh, concentrated or dried form, for example. These pharmaceutical products may be provided in the form of an ingestible suspension, a gel, a diffuser, a capsule, a hard gelatin capsule, a syrup, or in any other galenic form known to persons skilled in the art.

Figure 2:
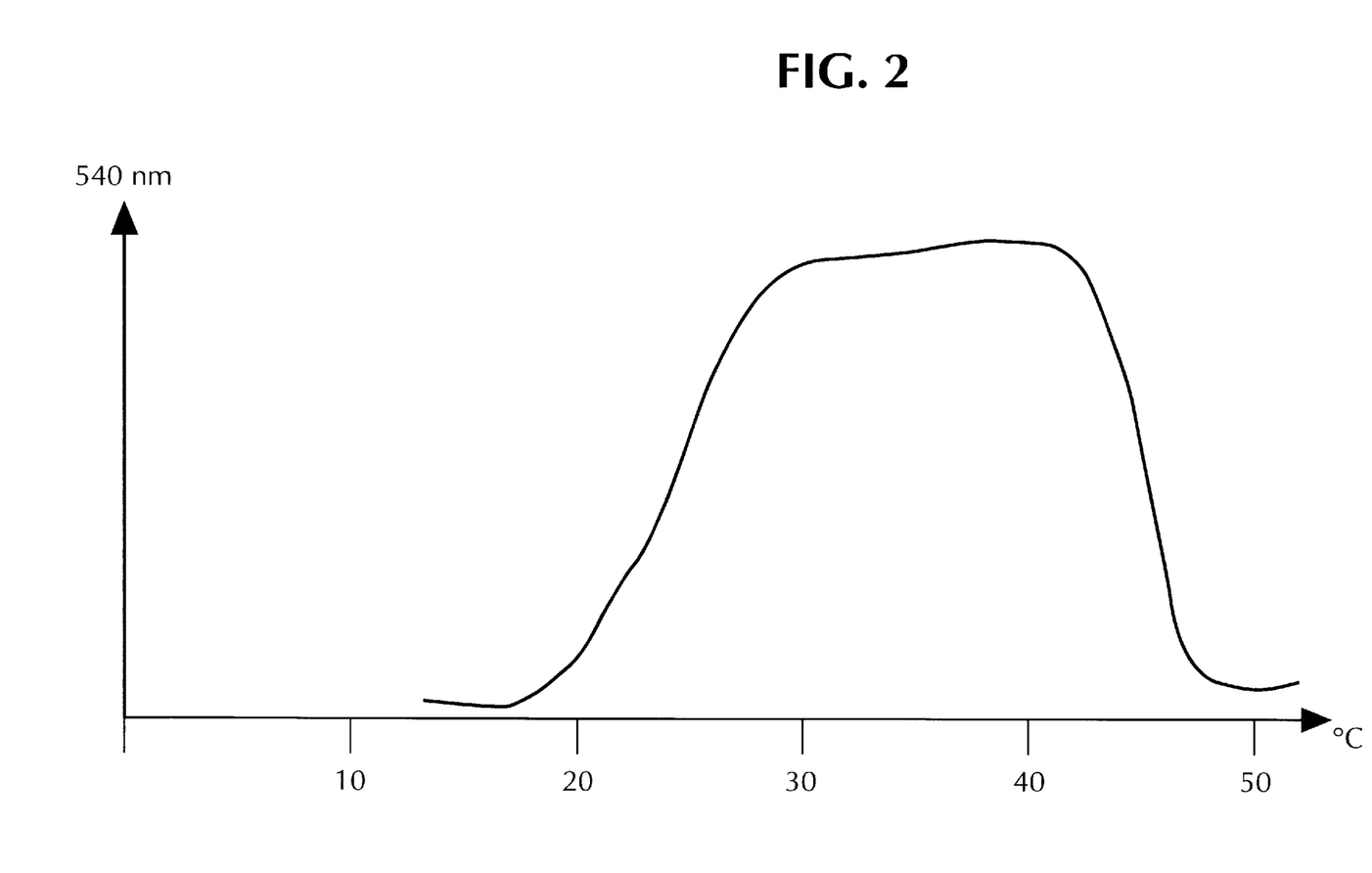
FIG. 2 is a depiction the graditherm for the strain CNCM I-1920.

Moreover, some strains of the new species according to the invention, representing a new biotype of this species, may also have the remarkable property of being both mesophilic and thermophilic (mesophilic/thermophilic biotype). The strains belonging to this biotype have a growth optimum from about 28° C. to about 45° C. This property can be easily observed (1) by preparing several cultures of a mesophilic/thermophilic biotype in parallel, at temperatures ranging from 20 to 50° C., (2) by measuring the absorbance values for the media after 16 h of culture, for example, and (3) by grouping the results in the form of a graph representing the absorbance as a function of the temperature (graditherm). FIG. 2 is particularly representative of the graphs which can be obtained with this type of mesophilic/thermophilic biotype according to the invention. As a guide, among the strains of the new species having this particular biotype, the strains CNCM I-1920, I-1921 and I-1922 are particularly representative, for example.

The use of a mesophilic/thermophilic biotype in the dairy industry is of great importance. Indeed, this species may be used for the preparation of mesophilic or thermophilic starters. It is thus possible to produce industrially acidified milks at 45° C. in order to obtain a "yogurt" type product. It is also possible to industrially produce cream cheese by fermenting a milk in the presence of rennet at 28° C., and separating therefrom the curd thus formed by centrifugation or ultrafiltration. The problems of clogging of the machines linked to the use of thermophilic ferments are thus eliminated (these problems are disclosed in patent application EP No. 96203683.6).

Moreover, other strains of the new species according to the invention, representing another new biotype of this species, may exhibit the remarkable property of conferring viscosity to the fermentation medium (texturing biotype). The viscous character of a milk fermented by a texturing biotype according to the invention may be observed and determined as described below:

1. Comparison of the structure of a milk acidified by a texturing biotype in comparison with that of milk acidified by non-texturing cultures; the non-viscous milk adheres to the walls of a glass cup, whereas the viscous milk is self-coherent.
2. Another test may be carried out using a pipette. The pipette is immersed in the acidified milk which is drawn up in a quantity of about 2 ml, and then the pipette is withdrawn from the milk. The viscous milk forms a rope between the pipette and the liquid surface, whereas the non-viscous milk does not give rise to this phenomenon. When the liquid is released from the pipette, the non-viscous milk forms distinct droplets just like water, whereas the viscous milk forms droplets ending with long strings which go up to the tip of the pipette.
3. When a test tube filled up to roughly a third of a rotary shaker, the non-viscous milk climbs up the inner surface of the wall, whereas the rise of the viscous milk is practically zero.

The viscous character of this particular biotype may also be determined with the aid of a rheological parameter measuring the viscosity. A few commercial apparatus are capable of determining this parameter, such as the rheometer Bohlin VOR (Bohlin GmbH, Germany). In accordance with the manufacturer's instructions, the sample is placed between a plate and a truncated cone of the same diameter (30 mm, angle of 5.4°, gap of 0.1 mm), then the sample is subjected to a continuous rotating shear rate gradient which forces it to flow. The sample, by resisting the strain, develops a tangential force called shear stress. This stress, which is proportional to the flow resistance, is measured by means of a torsion bar. The viscosity of the sample is then determined, for a given shear rate, by the ratio between the shear stress (Pa) and the shear rate ($s^{-1}$) (see also "Le Technoscope de Biofutur", May 97).

The tests of rheological measurement of the texturing character of this biotype have led to the following definition. A lactic acid bacterium belonging to the texturing biotype according to the invention is a bacterium which, when it ferments a semi-skimmed milk at 38° C. up to a pH of 5.2, gives to the medium a viscosity which is greater than 100 mPa.s at a shear rate of the order of 293 $s^{-1}$, for example. As a guide, the strains CNCM I-1922, I-1923, I-1924, I-1925 and I-1926 are particularly representative of this texturing biotype for example.

This texturing biotype is also of great importance in the dairy industry because its capacity to give viscosity to a dairy product is exceptionally high when it is compared with those of other species of texturing lactic acid bacteria, in particular with the strains *Lactobacillus helveticus* CNCM I-1449, *Streptococcus thermophilus* CNCM I-1351, *Streptococcus thermophilus* CNCM I-1879, *Streptococcus thermophilus* CNCM I-1590, *Lactobacillus bulgaricus* CNCM I-800 and *Leuconostoc mesenteroides ssp. cremoris* CNCM I-1692, which are mentioned respectively in patent applications EP 699689, EP 638642, EP 97111379.0, EP 750043, EP 367918 and EP 97201628.1.

It is also possible to note that the production of a viscosity may also take place, for some strains, in a very broad temperature range which extends from the mesophilic temperatures (25–30° C.) to the thermophilic temperatures (40–45° C.). This characteristic feature represents an obvious technological advantage.

However, some strains belonging to this new texturing biotype produce, moreover, an exopolysaccharide (EPS) of high molecular weight whose sugar composition is similar to that found in the oligosaccharides in human breast milk. The EPS in fact consists of a chain of glucose, galactose and N-acetylglucosamine in a proportion of 3:2:1 respectively (A. Kobata, in the Glycoconjugates, Vol. 1, "Milk glycoproteins and oligosaccharides", p. 423–440, Ed. I. Horowitz and W. Pigman, Ac. Press, N.Y., 1977). As a guide, the strains CNCM I-1923, I-1924, I-1925 and I-1926 produce this polysaccharide.

This exopolysaccharide, in native or hydrolyzed form, could thus advantageously satisfy a balanced infant diet.

For that, it is possible to prepare a diet for children and/or breast-feeding infants comprising a milk which has been acidifed with at least one strain of lactic acid bacterium producing an EPS consisting of a chain of glucose, galactose and N-acetylglucosamine in a proportion of 3:2:1, respectively, in particular with the strains CNCM I-1924, I-1925 or I-1926, for example.

It is also possible to isolate this EPS beforehand from a culture medium of this biotype, and to use it, in native or hydrolysed form, as ingredient in an infant diet, for example.

The isolation of the EPS generally consists in removing the proteins and the bacteria from the culture medium and in isolating a purified fraction of the EPS. It is also possible to carry out the extraction of the proteins and of the bacteria by precipitation with an alcohol or trichloroacetic acid followed by centrifugation, while the EPS can be purified by precipitation in a solvent such as acetone followed by centrifugation, for example. If necessary, the EPS may also be purified, for example, by means of gel-filtration or affinity chromatography.

In the context of the present invention, the isolation of an EPS also encompasses all the methods of production of an EPS by fermentation followed by concentration of the culture medium by drying or ultrafiltration, for example. The concentration may be performed by any method known to a person skilled in the art, and in particular by freeze- drying or spray-drying in a stream of hot air, for example. To this effect, the methods described in U.S. Pat. No. 3,985,901, EP 298605 and EP 63438 are incorporated by reference into the description of the present invention.

Insofar as the maternal oligosaccharides are small in size, it may be advantageous to carry out beforehand a partial hydrolysis of the EPS according to the invention. Preferably, the hydrolysis conditions are chosen so as to obtain oligosaccharides having 3 to 10 units of sugar, that is to say therefore oligosaccharides having a molecular weight on the order of 600 to 2000 Dalton, for example.

More particularly, it is possible to hydrolyze the EPS according to the invention in a 0.5 N trifluoroacetic acid (TFA) solution for 30–90 min at 100° C., and then to evaporate the TFA and to recover the oligosaccharides.

A preferred infant product comprises hydrolyzed protein material of whey from which allergens, chosen from a group consisting of alpha-lactalbumin, beta-lactoglobulin, serum albumin and the immunoglobulins, have not been removed and in which the hydrolysed protein material, including the hydrolysed allergens, exist in the form of hydrolysis residues having a molecular weight not greater than about 10,000 Dalton, such that the hydrolysed material is substantially free of allergenic proteins and of allergens of protein origin (=hypoallergenic product in accordance with European Directive 96/4/EC; Fritsche et al, *Int. Arch. Aller and Appl. Imm.*, 93, 289–293, 1990).

It is possible to mix the EPS according to the invention, in native or partially hydrolysed form, with this hydrolyzed protein material of whey, and to then incorporate this mixture, in dried form or otherwise, into numerous food preparations for dietetic use, in particular into foods for breast-feeding infants and into foods which can be easily absorbed, intended primarily for people suffering from allergies, for example.

The present invention is described in greater detail by the examples presented below, which are preceded by a brief description of the figures. It goes without saying however, that these examples are given by way of illustration of the subject of the invention and do not constitute in any manner a limitation thereto. The percentages are given by weight unless otherwise stated.

EXAMPLES

Example 1

Identification of a New Species of Streptococcus

Several strains of lactic acid bacteria isolated from various dairies in Switzerland were the subject of the following genetic and physiological identification. The methods used as well as the results obtained, which are represented below, show that these strains are part of a new Streptococcus group which is sufficiently distinct and homogeneous for it to be designated as grouping together a new species of lactic acid bacterium. By way of example, some strains belonging to this new species were deposited under the treaty of Budapest in the Collection Nationale de Culture de Microorganismes (CNCM), 25 rue du docteur Roux, 75724 Paris, on Oct. 14, 1997, where they received the identification Nos. CNCM I-1920, I-1921, I-1922, I-1923, I-1924, I-1925 and I-1926.

1. Morphology of the strains isolated: A morphology characteristic of the *Lactococcus lactis*, that is to say a shape of cocci assembled into chains, was observed under a microscope.

2. Sugar fermentation profile of the strains isolated: The sugars which can be fermented by the isolated strains are generally D-galactose, D-glucose, D-fructose, D-mannose, N-acetyl-(D)-glucosamine, salicin, cellobiose, maltose, lactose, sucrose and raffinose. This fermentation profile was similar to that obtained with the species *Lactococcus lactis*.

3. 16S ribosomal RNA of the strains isolated: The isolated strains were cultured in 40 ml of HJL medium at 37° C. for 24 h, the bacteria were harvested by centrifugation, each bacterial pellet was resuspended in 2.5 ml of TE buffer (10 mM Tris PH 8, 0.1 mM EDTA) containing 10 mg/ml of lysozyme, and the whole was incubated at 37° C. for 1 h. 100 $\mu$l of a solution containing 10 mg/ml of proteinase K, 250 $\mu$l of a solution containing 500 mM EDTA pH 8.0, and 500 $\mu$l of a solution containing 10% SDS was then added. The whole was incubated at 60° C. for 1 h so as to ensure complete lysis of the bacteria. After having cooled the mixtures, 2.5 ml of phenol/chloroform was added, and they were centrifuged for 10 min in a Heraeus centrifuge so as to separate 2 phases. The top phase was removed. The chromosomal DNA present in the bottom phase was precipitated by addition of 2.5 ml of a solution containing 96% ethanol, and the mixture was gently stirred until a precipitate was formed. The precipitated DNA was removed with the aid of a wooden toothpick, deposited in a 2 ml Eppendorf tube containing 1 ml of a Tris buffer (10 mM Tris HCl pH 8.0, 10 mM EDTA and 10 µg/ml of RNase A), and incubated at 56° C. for 1 h. After cooling, the various suspensions of DNA were extracted with 1 ml of phenol/chloroform as described above, and the chromosomal DNA was precipitated with ethanol. The DNA was resuspended in an Eppendorf tube containing a quantity of TE buffer such that the final quantity of DNA for each strain isolated was about 250 µg/ml.

An aliquot of 1 µl of DNA of each strain isolated was amplified by PCR with the primers having the respective nucleotide sequences SEQ ID NO: 2 and SEQ ID NO: 3 (see sequence listing), for 30 cycles (95° C./30 see, 40° C./30 sec and 72° C./2 min) using Pwo polymerase from Boebringer. The PCR products were purified with the aid of the QIAGEN QIAquick kit, and the products were eluted in 50 µl of TE buffer. A sample of 20 µl of each product was digested with the restriction enzymes BamHI and SalI, and the 1.6 kb fragments were separated on an agarose gel (1%), and purified with the aid of the QIAGEN QlAquick kit. The fragments were then cloned into the *E. coli* vector pK19 (R. D. Pridmore, Gene 56, 309–312, 1987) previously digested with BamHI and SalI and dephosphorylated, and competent cells of *E. coli* strain BZ234 (University of Basel collection, Switzerland) were transformed with each ligation product. The transformants were selected for at 37° C. on LB medium with 50 µg/ml of kanamycin, 30 ng/ml of X-gal and 10 ng/ml of IPTG. The white colonies containing the insert were cultured for 10 h on LB medium with 50 µl/ml of kanamycin, and the plasmid DNAs were isolated with the aid of the QIAGEN QlAprep8 kit.

A 4 µl sample of each plasmid (1 pmol/µl: obtained from each strain isolated) were mixed with 4 µl of labelled primers IRD-41 (sequencing primers: MWG Biotech) and 17 µl of $H_2O$. For each strain isolated, 4 aliquots of 6 µl were added to 4 wells of 200 µl , and 2 µl of a reaction mixture (Amersham; RPN2536) was then added to the wells. The mixtures were amplified by PCR in the Hybaid Omn-E system with 1 cycle of 95° C.for 2 min followed by 25 cycles of 95° C./30 sec, 50° C./30 sec and 72° C/1 min. The reaction product were then separated conventionally on a polyacrylamide gel, and the DNA sequence was determined for each isolated strain. The DNA fragments thus sequenced represented the genomic part of the 16S ribosomal RNA.

The results show that all the strains isolated contain a nucleotide sequence similar, or even identical, to the sequence identified in SEQ ID NO: 1 which is disclosed in the sequence listing. These sequences exhibit numerous homologies with the 16S RNA sequences found in the species of lactic acid bacteria belonging to the genus Streptococcus, which leads to these strains being classified in the genus Streptococcus.

4. Identification by SDS-PAGE electrophoresis gel: The tests were carried out in accordance with the instructions provided by Pot et al., presented during a "workshop" organized by the European Union, at the University of Ghent, in Belgium, on Sep. 12 to 16, 1994 (Fingerprinting techniques for classification and identification of bacteria, SDS-PAGE of whole cell protein).

In short, to cultivate the lactic acid bacteria, 10 ml of MRS medium (of Man, ogosa and Sharpe) are inoculated with an MRS preculture of each strain of the new species of lactic acid baterium, as well as of each reference strain covering as many species of Streptococcus as possible. The media are incubated for 24 h at 28° C., they are plated on a Petri dish comprising a fresh MRS-agar medium, and the dishes are incubated for 24 h at 28° C.

To prepare the extract containing the proteins of the bacteria, the MRS-agar medium is covered with a pH 7.3 buffer containing 0.008 M of $Na_2HPO_4 \cdot 12H_2O$, 0.002 M of $Na_2HPO_4 \cdot 2H_2O$ and 8% NaCl. The bacteria are recovered by scraping the surface of the gelled medium, the suspension is filtered through a nylon gauze, it is centrifuged for 10 min at 9000 rpm with a GSA rotor, the pellet is recovered and taken up in 1 ml of the preceding buffer. The pellet is washed by repeating the centrifugation-washing procedure, finally about 50 mg of cells are recovered to which one volume of STB buffer pH 6.8 (per 1000 ml: 0.75 g Tris, 5 ml $C_2H_6OS$, 5 g of glycerol) is added, the cells are broken by ultrasound (Labsonic 2000), the cellular debris is centrifuged, and the supernatent containing the total a protein is preserved.

An SDS-PAGE polyacrylamide gel 1.5 mm thick (Biorad-Protean or Hoefer SE600), crosslinked with 12% acrylamide in the case of the separating gel (12.6 cm in height) and 5% acrylamide in the case of the stacking gel (1.4 cm in height), is then conventionally prepared. For that, the polymerization of the two gel parts is carried out in particular in a thermostated bath at 19° C. for 24 h and 1 h respectively, so as to reduce the gel imperfections as much as possible and to maximize the reproducibility of the tests.

The proteins of each extract are then separated on the SDS-PAGE electrophoresis gel. For that, 6 mA are applied for each plate containing 20 lanes until the dye reaches a distance of 9.5 cm from the top of the separating gel. The proteins are then fixed in the gel, they are stained, the gel is dried on a cellophane, the gel is digitized by means of a densitometer (LKB Ultroscan Laser Densitometer, Sweden) linked to a computer, and the profiles are compared with each other by means of the GelCompar® software, version 4.0, Applied Maths, Kortrijk, Belgium. Insofar as the tests were sufficiently standardized, the profiles of the various species of Streptococcus contained in a given library were also used during the digital comparison.

The results then show that all the strains tested belonging to the new species can be distinguished from all of the following species: *S. acidominimus, S. adjacens, S. agalactiae, S. alactolyticus, S. anginosus, S. bovis, S. canis, S. caprinus, S. casseliflavus, S. cecorum, S. constellatus, S. cremoris, S. cricetus, S. cristatus, S. defectivus, S. difficile, S. downei, S. dysgalactiae* ssp. *dysgalactiae, S. dysgalactiae* ssp. *equisimilis, S. equi, S. equi* ssp. *equi, S. equi* ssp. *zooepidemicus, S. equinus, S. faecalis, S. faecium, S. ferus, S. gallinarum, S. gallolyticus, S. garvieae, S. gordonii, S. hansenii, S. hyointestinalis, S. hyovaginalis, S. iniae, S. intermedius, S. intestinalis, S. lactis, S. lactis cremoris, S. lactis diacetilactis, S. macacae, S. mitis, S. morbillorum, S. mutans, S. oralis, S. parasanguinis, S. parauberis, S. parvulus, S. phocae, S. plantarum, S. pleomorphus, S. pneumoniae, S. porcinus, S. pyogenes, S. raffinolactis, S. ratti, S. saccharolyticus, S. salivarius, S. sanguinis, S. shiloi, S. sobrinlus, S. suis, S. thermophilus, S. thoraltensis, S. uberis, S. vestibularis* and *S. viridans*.

Figure 1:
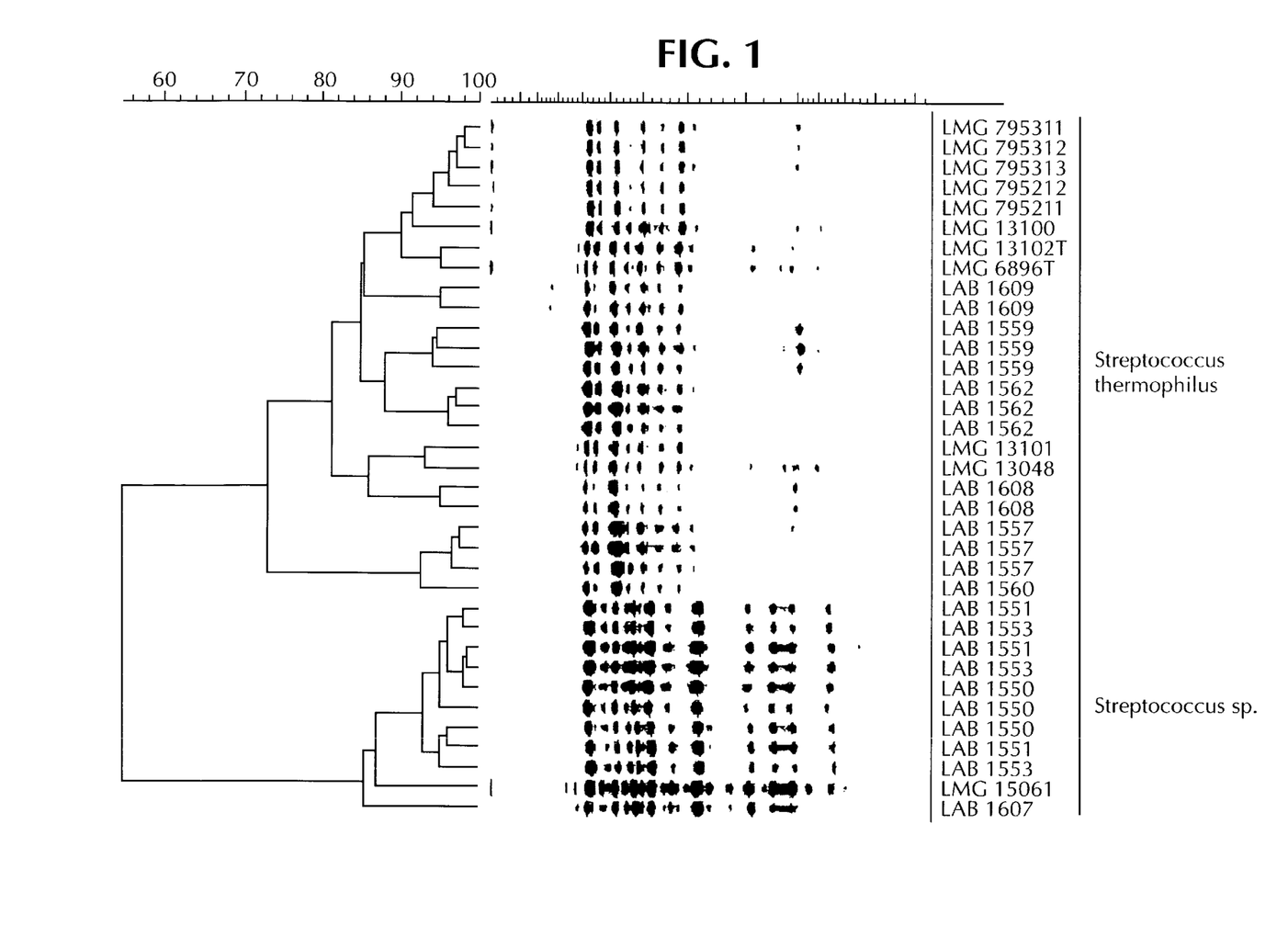
FIG. 1 is a photographic depiction of the migration profiles of the total proteins of several strains of the new species, on an SDS-PAGE electrophoresis gel, in comparison with those obtained with *Streptococcus thermophilus* strains. The degree of filiation of the strains is indicated with the aid of the Pearson correlation scale and by means of a tree opposite the protein profiles (the degrees of Pearson correlation of 55 to 100 are represented).

All the results show that the degree of Pearson correlation between the strains deposited is at least 85. As a guide, FIG. 1 depicts a photograph of one of the electrophoresis gels, the filiation in the form of a tree, as well as the degree of Pearson correlation (indicated on the top left-hand scale). The strains LAB 1550, LAB 1551 and LAB 1553 refer specifically to the strains CNCM I-1921, I-1922 and I-1925. The strains LMG15061 and LAB 1607 were not deposited at the CNCM, but obviously form part of this new species.

In short, all the strains isolated clearly form part of a homogeneous group, which is distinct from the other species belonging to the genus Streptococcus.

Example 2

Mesophilic/thermophilic Biotype

Some strains isolated in Example 1 represent a new particular biotype since they exhibit the remarkable property of being both mesophilic and thermophilic.

This property may easily be observed (1) by preparing, in parallel, several cultures of a mesophilic/thermophilic biotype in an M17-lactose medium at temperatures ranging from 20 to 50° C., (2) by measuring the absorbance values for the media at 540 nm after 16 h of culture, and (3) by grouping the results in the form of a graph representing the absorbance as a function of the temperature (graditherm).

FIG. 2 represents the graditherm obtained with the strain CNCM I-1920. All the other strains isolated belonging to this particular biotype, in particular the strains CNCM I-1921 and I-1922, also give comparable graditherms.

Example 3

Texturing Biotype

Several strains isolated in Example 1 had the remarkable property of being extremely texturing. This property was observed with the aid of the rheological parameter of viscosity measured with a Bohlin VOR rotational rheometer (Bohlin GmbH, Germany).

For that, some of the strains isolated were cultured in a semi-skimmed milk at 38° C. with a pH up to about 5.2. In accordance with the manufacturer's instructions, a sample of each culture medium was then placed between a plate and a truncated cone of the same diameter (30 mm, angle of 5.4°, gap of 0.1 mm), then the sample was subjected to a continuous rotating shear rate gradient which forces it to flow. The viscosity of the sample was then determined at a shear rate of 293 $s^{-1}$. The results of the rheology tests carried out with some of the strains isolated demonstarted that the culture media thus fermented had a viscosity greater than 100 mPa.s, or even a viscosity exceeding 200 mPa.s in the case of the strains CNCM I-1922, I-1923, I-1924, I-1925 and I-1926.

For comparison, viscosities of the order of 54, 94, 104, 158 and 165 mPa.s were obtained, under the same operating conditions, with the strains *Lactobacillus helveticus* CNCM I-1449, *Streptococcus thermophilus* CNCM I-1351, *Streptococcus thermophilus* CNCM I-1879, *Streptococcus thermophilus* CNCM I-1590, *Lactobacillus bulgaricus* CNCM I-800 and *Leuconostoc mesenteroides* ssp. *cremoris* CNCM I-1692, respectively, which were mentioned in patent applications EP 699689, EP 638642, EP 97111379.0, EP 750043, EP 367918 and EP 97201628.1, respectively (the strains CNCM I-800 and I-1692 were reputed to be highly texturing strains).

Example 4

New Exopolysaccharide

Some strains isolated in Example 1, belonging to the texturing biotype, in particular the strains CNCM I-1923, I-1924, I-1925 and I-1926, produced an EPS of high molecular weight whose sugar composition was similar to those found in certain oligosaccharides in human breast milk. Analysis of the sugars constituting this polysaccharide was carried out in the following manner.

The strains of the new species were cultured in 10% reconstituted skimmed milk, with shaking, for 24 h at 30° C., the pH being maintained at 5.5 by addition of a 2 N NaOH solution. The bacterial cells and the proteins were removed from the culture medium by means of precipitation in an equal volume of a solution of 25% by weight of trichloroacetic acid, followed by centrifugation (10,000 g, 1 h). The EPSs were precipitated by addition of an equivalent volume of acetone, followed by settling for 20 h at 4° C. The EPSs were recovered by centrifugation, and the pellet was taken up in a 0.1 M $NH_4HCO_3$ solution pH 7, and the suspension was dialyzed against water for 24 h. The insoluble materials were then removed by ultracentrifugation, and the retentate containing the purified EPS was freeze-dried. The quantity of purified EPS, expressed as mg of glucose equivalent, was on the order of 40 mg per litre of culture.

The molecular weight of the EPS was determined by means of gel-filtration chromatography with the aid of a Superose-6 column connected to an FPLC system (Pharmacia), as described by Stingele et al., J. Bacteriol., 178, 1680–1690, 1996. The results demonstrated that all the strains CNCM I-1923, I-1924, I-1925 and I-1926 produce an EPS of a size greater than $2\times10^6$ Da.

100 mg glucose equivalent of the purified EPS was hydrolyzed in 4 N TFA at 125° C. for 1 h, before being derivatized and analysed by GLC chromatography according to the method described by Neeser et al. (Anal. Biochem., 142, 58–67, 1984). The results demonstarted that the strains produced an EPS consisting of glucose, galactose and N- acetylglucosamine in a mean proportion of 3:2:1, respectively.

Example 5

Infant Product

A whey, 18% hydrolysed with trypsine is prepared according to the recommendations of U.S. Pat. No. 5,039,532. It is traditionally spray-dried in a stream of hot air, and between 0.1 and 10% of the dry purified EPS described in Example 4 is incorporated into it. This product can be rapidly reconstituted in water. It is particularly suitable for a diet for children or breast-feeding infants because of its hypoallergenic and tolerogenic properties to cow's milk, and because it is balanced from a carbohydrate composition point of view.

Example 6

Infant Product

The dry purified EPS of Example 4 is hydrolysed in a 0.5 N trifluoroacetic acid (TFA) solution for 30–90 min and at 100° C., the TFA is evaporated, the hydrolyzate is suspended in water and the oligosaccharides having 3 to 10 units of sugar (600 to 2000 Dalton) are separated by ultrafiltration.

A whey, 18% hydrolysed with trypsine is prepared according to the recommendations of U.S. Pat. No. 5,039,532. It is traditionally spray-dried in a stream of hot air, and between 0.1 and 10% of purified oligosaccharides described above is incorporated into it. This product can be rapidly reconstituted in water. It is particularly suitable for a diet for children or breast-feeding infants because of its hypoallergenic and tolerogenic properties to cow's milk, and because it is balanced from a carbohydrate composition point of view.

Example 7

Pharmaceutical Product

A pharmaceutical composition is prepared in the form of a capsule manufactured based on gelatin and water, and which contains 5 to 50 mg of the purified EPS of Example 4 or the purified oligosaccharides of Example 6.

Example 8

Pharmaceutical Product

Pastilles consisting of a culture of the freeze-dried strain CNCM I-1924 are prepared and then compressed with a suitable binding agent. These pastilles are particularly recommended for restoring an intestinal flora of lactic acid bacteria and for satisfying a balanced diet in terms of essential complex carbohydrates.

What is claimed is:

1. A biologically pure culture of a lactic acid bacteria strain having all the identifying characteristics of CNCM I-1923, I-1924, I-1925, or I-1926.

2. A dietary composition comprising a strain of lactic acid bacterium according to claim 1.

3. The dietary composition of claim 2, wherein the strain of lactic acid bacterium is selected from the group consisting of CNCM I-1924, I 1925, and I-1926.

4. The composition of claim 2, wherein the dietary composition is a milk-based product.

5. The composition of claim 4, wherein the milk-based product is a dietary or pharmaceutical composition comprising an exopolysaccharide.

6. The composition of claim 5, wherein the exopolysaccharide is a polysaccharide consisting of a chain of glucose, galactose and N-acetylglucosamine in a proportion of 3:2:1 respectively.

7. The composition of claim 6, wherein the milk-based product is an infant formula.

8. The composition of claim 5, wherein the milk-based product is a milk of animal or vegetable origin and is in a native state or is reconstituted or skimmed.

9. A biologically pure culture of a lactic acid bacteria strain having all the identifying characteristics of CNCM I-1920, I-1921 or I-1922.

10. A dietary composition comprising a strain of lactic acid bacterium according to claim 9.

11. The composition of claim 10, wherein the dietary composition is a milk-based product.

12. The composition of claim 11, wherein the milk-based product is acidified milk or fromage frais.

13. The composition of claim 11, wherein the milk-based product is a milk of animal or vegetable origin and is in a native state or is reconstituted or skimmed.

14. A biologically pure culture of a lactic acid bacteria strain having all the identifying characteristics of CNCM I-1922, I-1923, I-1924, 1 1925, or I-1926.

15. A dietary composition comprising a strain of lactic acid bacterium according to claim 14.

16. The composition of claim 15, wherein the dietary composition is a milk-based product.

17. The composition of claim 16, wherein the strain acts as a viscosity increasing agent for the product.

18. The composition of claim 6, wherein the milk-based product is a milk of animal or vegetable origin and is in a native state or is reconstituted or skimmed.

* * * * *

UNITED STATES PATENT AND TRADEMARK OFFICE
CERTIFICATE OF CORRECTION

PATENT NO.    : 6,579,711 B1
DATED         : June 17, 2003
INVENTOR(S)   : Gaier et al.

It is certified that error appears in the above-identified patent and that said Letters Patent is hereby corrected as shown below:

<u>Column 16,</u>
Line 27, change "1 1925" to -- I 1925 --.

Signed and Sealed this

Twenty-second Day of July, 2003

JAMES E. ROGAN
*Director of the United States Patent and Trademark Office*